United States Patent [19]
Rydell

[11] Patent Number: 5,163,942
[45] Date of Patent: Nov. 17, 1992

[54] SURGICAL INSTRUMENT WITH GRASPING LOOP FOR LAPAROSCOPIC PROCEDURES

[75] Inventor: Mark A. Rydell, Golden Valley, Minn.

[73] Assignee: Everest Medical Corporation, Minneapolis, Minn.

[21] Appl. No.: 804,248

[22] Filed: Dec. 9, 1991

[51] Int. Cl.⁵ .............................................. A61B 17/00
[52] U.S. Cl. .................... 606/113; 606/110; 606/1
[58] Field of Search ............ 606/1, 106, 110, 112, 606/113, 114, 127, 128, 135, 136, 137, 39, 45–50

[56] References Cited

U.S. PATENT DOCUMENTS

| | | | |
|---|---|---|---|
| 612,569 | 10/1898 | Muscap | 606/113 |
| 1,606,497 | 11/1926 | Berger | 606/113 |
| 3,181,533 | 5/1965 | Heath | 606/113 |
| 3,903,892 | 9/1975 | Komiya | 606/110 |
| 4,467,802 | 8/1984 | Maslanka | 606/127 |
| 4,741,335 | 5/1988 | Okada | 606/127 |
| 5,084,054 | 1/1992 | Bencini et al. | 606/113 |

FOREIGN PATENT DOCUMENTS

| | | | |
|---|---|---|---|
| 0027704 | 4/1981 | European Pat. Off. | 606/113 |
| 0152032 | 8/1985 | European Pat. Off. | 606/127 |
| 0772540 | 10/1980 | U.S.S.R. | 606/110 |
| 0029470 | of 1912 | United Kingdom | 606/113 |

Primary Examiner—Stephen C. Pellegrino
Assistant Examiner—Glenn K. Dawson
Attorney, Agent, or Firm—Haugen and Nikolai

[57] ABSTRACT

A surgical instrument for laparoscopic and endoscopic treatment of tissue and organs is disclosed. It includes a handle with a tubular member extending therefrom. Disposed within the tubular member and extending from the distal end thereof is an extendable and retractable grasping loop or belt, joined at its proximal ends to a slide assembly contained within the handle.

The slide member assembly includes a thumb loop, and finger grips mounted on the handle receive additional fingers of the surgeon. Proximal movement of the thumb loop withdraws the belt further into the tubular member to close the grasping loop, while distal movement extends the belt outward to form a flexible grasping loop at the distal end of the instrument to open it to encompass the organ or tissue.

The flexible grasping loop may be placed around an internal organ or tissue, then its grasp tightened by proximal movement of the thumb loop. Rotation of the organ during grasping may be achieved by either rotating the instrument about its longitudinal axis or by manipulation of a specialized rotator assembly mounted within the housing for turning the organ about an axis transverse to the longitudinal axis.

11 Claims, 3 Drawing Sheets

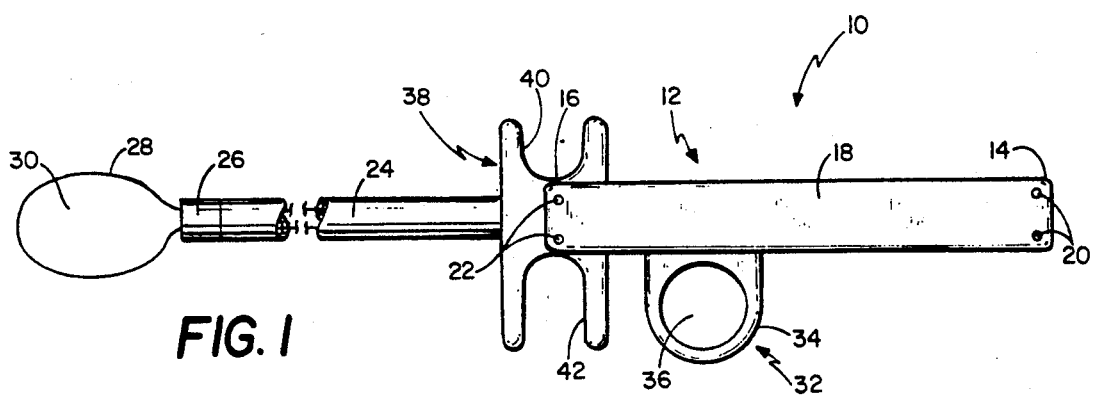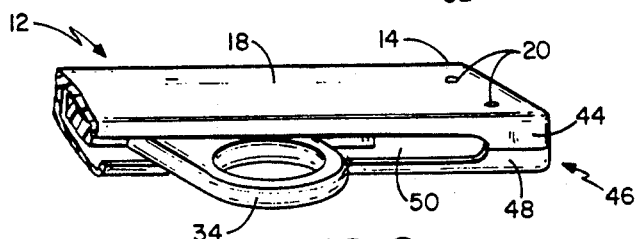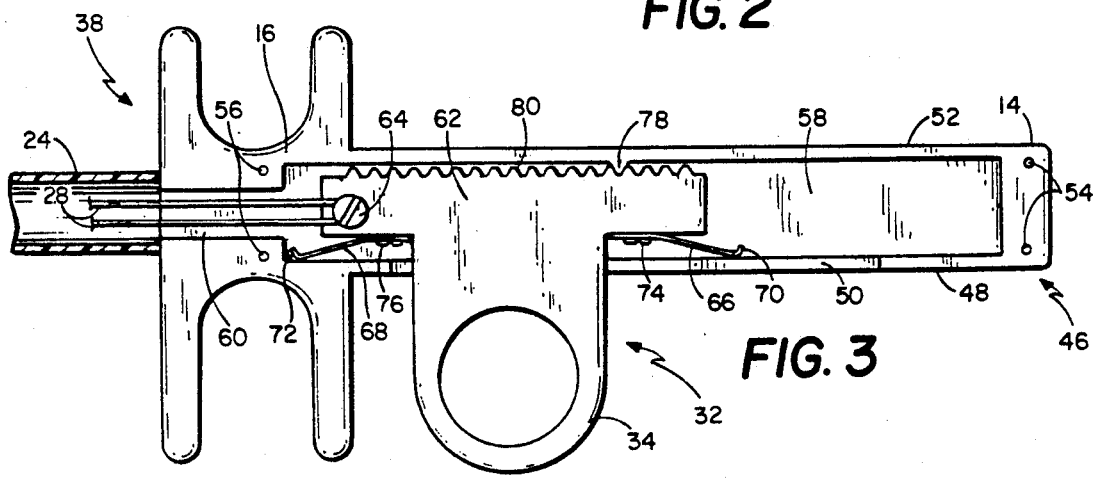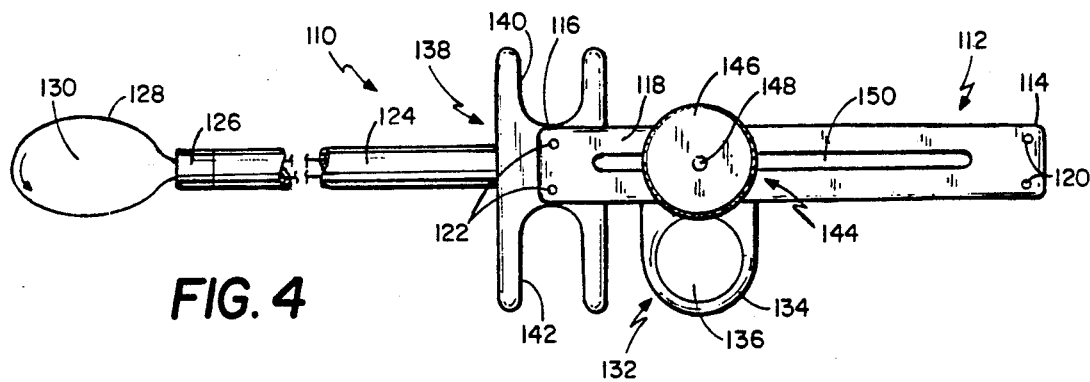

SURGICAL INSTRUMENT WITH GRASPING LOOP FOR LAPAROSCOPIC PROCEDURES

BACKGROUND OF THE INVENTION

I. Field of the Invention

This invention relates generally to surgical instruments used in laparoscopic or endoscopic procedures and, more particularly, to an instrument having a grasping loop for engaging and rotating an internal organ or tissue.

II. Discussion of the Prior Art

Gallbladder extraction is presently performed with a minimal amount of dissection. Typically, several small incisions are placed at epigastric, lateral and umbilical sites and extend through the abdomen to provide access to the liver bed. These incisions are no larger than necessary to receive conventional forceps, an endoscopic camera, a suction head, a laparoscopic trocar, or a cautery head. Typically, the endoscopic camera and cautery are used to assist in locating the cystic artery and duct during meticulous blunt dissection. After having been adequately ligated, they are divided using a laparoscopic scissors, also inserted through one of these incisions. The cautery is also used to assist in dissecting the gallbladder retrograde from the liver bed and to seal any small bleeding vessels. Occasionally, subphrenic fluid may collect in this region, and it is removed by aspiration using the suction head inserted through another incision.

During the retrograde cauterization of the gallbladder, it is frequently desirable to twist and otherwise manipulate the tissue to expose all regions for dissection. In the prior art, a large grasping forceps is inserted through the umbilical incision to assist in maneuvering tissue and, if possible, large stones are crushed with the blades of the forceps. The gallbladder is then withdrawn through that incision. When extremely large stones are present or when there are multiple impacted stones, the infundibulum is incised and the gallbladder is decompressed using suction. Thus, using these specialized instruments, a procedure which formally required major abdominal surgery and an extended recovery has now been reduced to a few small incisions and minimal recovery.

Despite these great advances, it is occasionally difficult to grasp and retract or otherwise manipulate the gallbladder prior to severance from the liver bed using presently available instruments. For example, using presently available instruments, such as the aforementioned forceps, it is sometimes difficult to rotate the gallbladder to obtain improved access to the disection plane without inadvertently lacerating the gallbladder.

It is accordingly a principal object of the present invention to provide a new and improved surgical instrument for grasping an organ such as the gallbladder during laparoscopic procedures.

Another object of the present invention is to provide a new and improved method and apparatus for grasping and rotating an internal organ with precision.

It is yet another object of the present invention to provide a new and improved method and apparatus for controllably rotating an organ while simultaneously providing traction.

A still further object of the present invention is to provide a new and improved handle for a laparoscopic surgical instrument which is low in cost and easy to use.

SUMMARY OF THE INVENTION

The foregoing objects and advantages of the invention are achieved by providing a laparoscopic surgical instrument having a surgeon-manipulated grasping loop at its distal end. The loop is used to encircle small internal organs, such as the gallbladder, to grasp the organ, rotate it about the longitudinal axis of the instrument and to tension and retract the organ as it is surgically excised. A significant advantage attendant to the construction of the preferred embodiment when compared to the prior art is that it is light-weight and comprised of simple, easily molded components. An alternative embodiment provides a loop rotator assembly which is used to rotate the loop and the ensnared organ about an axis transverse to the longitudinal axis of the instrument.

This improved surgical instrument may be comprised entirely of molded plastic and, thus, is significantly easier to produce with less expensive materials than the prior art. Consequently, the present device is totally disposable, avoiding the need for meticulous cleaning and sterilization following use. The plastic belt or cord which forms the loop may be serrated or otherwise roughened on the surface that contacts tissue, to enhance friction between the surfaces and improve grasping within the loop.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE DRAWINGS

FIG. 1 shows a side elevation view of a preferred embodiment of the laparoscopic surgical instrument of the present invention;

FIG. 2 shows a partial, perspective, bottom view of the proximal end of the laparoscopic surgical instrument of FIG. 1;

FIG. 3 shows an enlarged, side elevation view of the proximal end of the embodiment of FIG. 1 with the cover plate removed;

FIG. 4 shows a side elevation view of an alternative embodiment of the laparoscopic surgical instrument of the present invention;

DESCRIPTION OF THE PREFERRED EMBODIMENT

Figure 5:
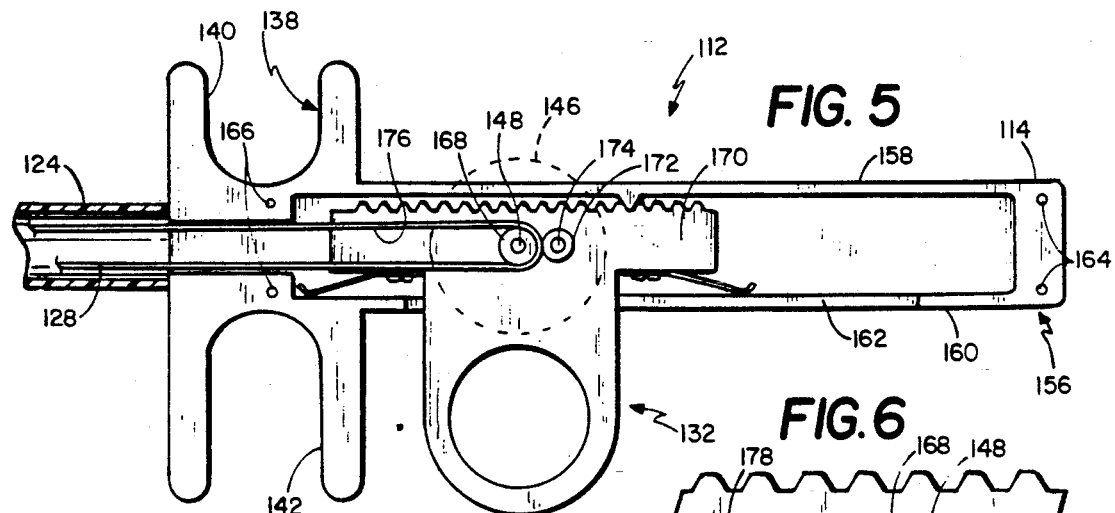
FIG. 5 is an enlarged, side elevation view of the proximal end of the embodiment of FIG. 4.

Referring to FIG. 1, there is indicated generally by numeral 10 the endoscopic or laparoscopic grasping instrument constructed in accordance with the present invention. It is seen to include a handle member, generally designated 12, which is preferably formed of molded and rigid medical grade plastic material. The handle member 12 has a proximal end 14 and a distal end 16. As best seen in this view, it includes a cover plate 18 held in place by screws 20 and 22.

Extending distally from handle member 12 is an elongated, semi-rigid tubular member 24. A hub 26 is positioned at its distal end, from which extends belt 28 of narrow width, formed into grasping loop 30. While a narrow width belt is perhaps preferred because it is less likely to cut into the tissue being grasped, it is also possible to use a cord or fine cable of generally circular cross-section for creating the grasping loop. Although not depicted in this view, a divider may be placed within hub 26 to separate the portions of the belt 28 that extend therethrough The handle member 12 further includes a slide member assembly, generally designated 32. Although portions of the slide member assembly 32 are more clearly shown in FIG. 3, which depicts the handle 12 with its cover plate 18 removed, FIG. 1 shows a thumb loop 34 extending outward from handle member 12. The thumb loop is molded to include a central opening 36 into which a thumb or finger may be inserted.

Positioned at the distal end 16 of handle member 12 is a stationary finger grip assembly, generally designated as 38. The finger grip assembly 38 includes finger slots 40 and 42, which are dimensioned to comfortably receive the surgeon's fingers during use.

FIG. 2 provides a perspective bottom view of a portion of the proximal end of the handle member 12. In this view, the edge 44 of the cover plate 18 is more clearly seen to be rigidly affixed to the instrument frame, generally designated 46. The bottom 48 of the instrument frame 46 includes a slot 50 dimensioned to receive the thumb loop 34 through it with a predetermined clearance fit. As further explained in reference to FIG. 3, the thumb loop 34 may be displaced distally or proximally within slot 50.

FIG. 3 shows an enlarged, side elevation view of the proximal end of the surgical instrument 10 with cover plate 18 removed to expose the instrument frame 46. It is apparent in this view that the bottom 48 and the top 52 of the instrument frame 46 is molded or etched from a solid piece of plastic including the finger grip assembly 38. Screw holes 54 and 56 are drilled in instrument frame 46 to receive the screws 20 and 22, which secure cover plate 18. The instrument frame 46 is molded to further include a back wall 58, thus forming a void or hollow region between the top 52, bottom 48 and back wall 58. At the distal end 16, the frame 46 is molded to form a channel 60 between this void and the elongated tubular member 24. The belt 28 is disposed within this channel and may have a smooth inner surface or, for enhanced friction during grasping, it may be serrated or otherwise roughened. Its two halves are fastened to a slide member plate 62 by a fastener 64 and extend through the channel 60 in parallel orientation toward loop 30.

The slide member plate 62 is molded or otherwise formed as a unit with thumb loop 34, comprising slide member assembly 32. Extending toward the instrument frame bottom 48 from the slide member plate 62 are a pair of leaf springs 66 and 68, which are angled at their ends 70 and 72 in the conventional manner. The leaf springs 66 and 68 are preferably made of phosphor-bronze and are held against the slide member plate 62 by screws 74 and 76. An inwardly projecting detent tooth 78 is formed on the inner wall of the top 52 of the instrument frame. It is dimensioned appropriately to mesh with a serrated edge 80 that is included on the upper edge of plate 62 of the slide member assembly 32.

In operation, a surgeon grasps the laparoscopic surgical instrument 10 at the handle member 12 and inserts the loop 3 through a laparoscopic trocar or directly through an incision in the patient's skin. The elongated tubular member 24 is preferably formed from semi-rigid plastic and dimensioned to include sufficient length that loop 30 may easily access internal organs to be grasped and manipulated. Preferably, tubular member 24 has an outer diameter in the range from 0.190 to 0.205 inch. With a thumb positioned within opening 36 of slide member assembly 32, and two fingers disposed in finger slots 40 and 42, the slide member assembly 32 may be caused to move proximally and distally within slot 50. When a downward force is exerted by the thumb on thumb loop 34, the leaf springs 66 and 68 are compressed, disengaging the detent tooth 78 from the serrations 80 in the slide. As the thumb loop 34 is drawn toward the proximal end 14 of the instrument, the belt 28 is withdrawn into the elongated tubular member 24, closing the loop 30. The slide member assembly is locked in the new position when the downward pressure is released, allowing detent tooth 78 to mesh with the serrated edge 80. When the thumb loop 3 is displaced distally, the belt 28 is advanced through the lumen 84 of tubular member 24 and the loop 30 expands. In this expanded position, the loop may be placed about an internal organ such as a gallbladder. Once in place, proximal displacement of the thumb loop 34 will tighten the loop 30 around the organ. The organ may now be twisted and/or placed in traction by appropriate manipulation of the instrument. Treatment may include cauterizing, dissecting, or otherwise manipulating the organ. Manual rotation of handle member 12 is translated to loop 30, permitting twisting of the organ or transverse rotation about the longitudinal axis of the instrument.

An alternative embodiment of the laparoscopic surgical instrument which provides for rotation of the grasped organ is shown in FIG. 4. The instrument, generally designated 110, also includes a handle member 112 having a proximal end 114 and a distal end 116. A cover plate 118 is held with screws 120 and 122 to the one-piece base of the instrument, analogous to the attachment shown in FIG. 2. An elongated tubular member 124, terminating in hub 126, extends from the handle member 112 and provides a housing for a flexible belt, cord or cable 128, which forms grasping loop 130. With no limitation to a particular size intended, belt 128 may be approximately 0.125 inch wide. Slide member assembly 132 includes a thumb loop 134 having central opening 136 dimensioned to receive a finger or thumb of the surgeon. A stationary finger grip assembly, generally designated 138 includes finger slots 140 and 142.

Figure 6:
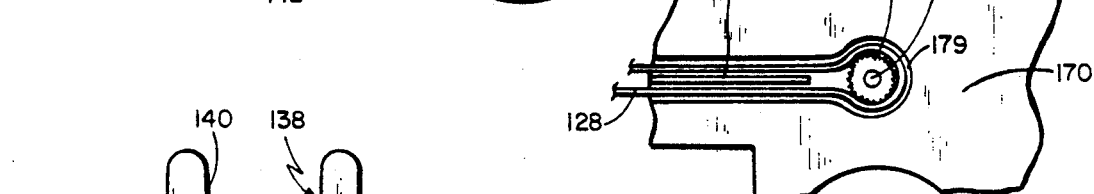
FIG. 6 is an enlarged, partial, side elevation view of an alternative roller system for the embodiment of FIG. 5.
Figure 7:
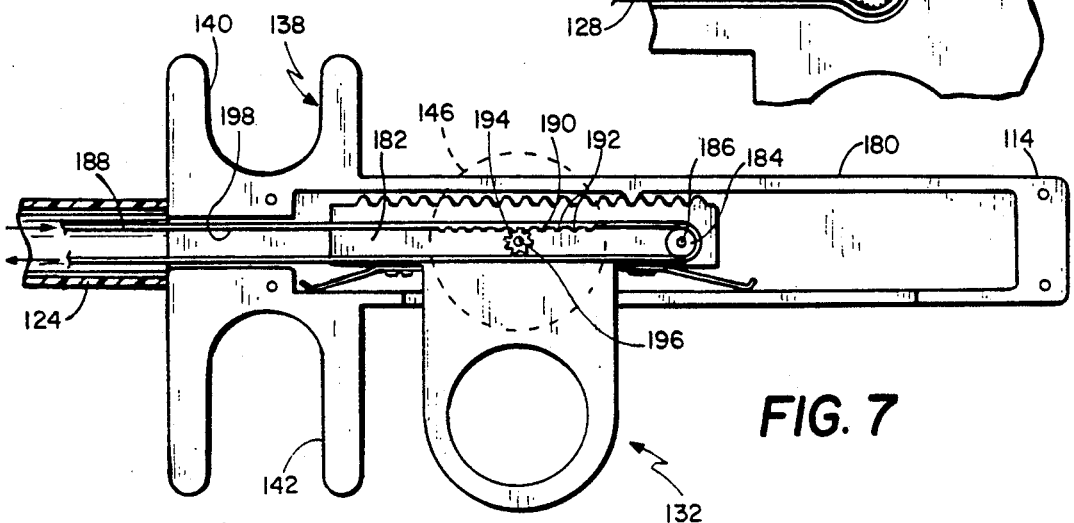
FIG. 7 is an enlarged, side elevation view of an alternative embodiment of the proximal end of the laparoscopic surgical instrument of FIG. 5.
Figure 8:
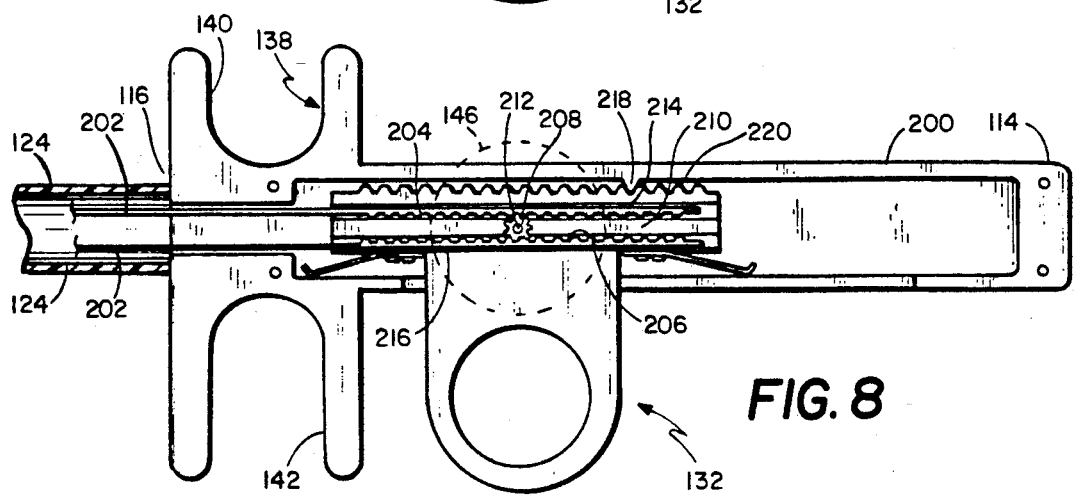
FIG. 8 is an enlarged, side elevation view of another alternative embodiment of the proximal end of the laparoscopic surgical instrument of FIG. 5.

Although described more fully in the descriptions provided herein for FIGS. 6 through 8, a loop rotator assembly, generally designated 144, is provided on handle member 112. The rotator assembly 144 includes a knob 146, which is preferably knurled to facilitate being grasped, and is held in place on slide member assembly 132 with a shaft 148. A slot 150 is provided in cover plate 118 to permit the shaft 148 to be moved proximally and distally as the thumb loop 134 is moved.

An enlarged view of the handle member 112 is shown in FIG. 5. The frame or base member of the instrument, generally designated 156, is constructed in a manner similar to that of FIG. 1 and includes a top wall 158 and a bottom wall 160, the bottom wall having an elongated slot 162, to receive the slide member assembly 132 therealong. Screw holes 164 and 166 receive the screws 120 and 122 upon attachment of the rectangular cover plate 118 (FIG. 4). In contrast to the embodiment of FIG. 1, the belt 128 may be formed in a continuous loop. Although permitted to extend from hub 126 to form loop 130, the portion inserted within handle member 112 is wrapped around a drive roller 168. Drive roller 168 is keyed to the shaft 148 of knob 146 (in shadow) which, in turn, is journaled for rotation on slide member plate 170. Pressure between the belt and drive roller 168 is provided by an idler roller 172, held to plate 170 by pin 174.

In operation, and with reference to FIG. 4, clockwise rotation of knob 146 also rotates drive roller 168 in a clockwise direction, causing flight of the section of belt 128 that is adjacent to the bottom 160 of the frame 156 to be moved in the proximal direction. Concomitantly, a commensurate portion of belt 128 is advanced along the top 188 of the frame in the distal direction. If pressure within the grasping loop has not been released by movement of the slide member assembly 132, this movement of the belt 128 causes the organ grasped within loop 130 to be rotated due to friction between the belt and the organ in the direction indicated by the arrow within the loop in FIG. 4. One skilled in the art will recognize that belt 128 may have a smooth surface adjacent to drive roller 168, or the surface may include small teeth 176, which will contact both the external surface of the drive roller and the external surface of the organ held within the loop, thus facilitating rotation.

FIG. 6 provides an alternative roller apparatus that dispenses with any need for an idler roller. A recess 178 is molded or bored into slide member plate 170. The recess 178 is slightly larger than the space occupied by roller 168 and belt 128, to permit movement of the belt while keeping it in close engagement with the toothed drive roller. A spacer 179 is placed between the sections of the belt 128 that lead to and from the drive roller. The spacer 179 keeps the notches or roughened surface on the belt from rubbing against one another.

An alternative apparatus for rotating the loop 130 is shown enlarged in FIG. 7. The slide member assembly 132 and finger grip assembly 138 are also constructed in a manner similar to the corresponding portions of the embodiment of FIG. 1, as is the instrument housing or frame 180. The slide member assembly includes plate 182 upon which is mounted pulley 184, journaled with pin 186. Belt 188 wraps around rotatable pulley 184 within frame 180 and extends through tubular member 124 to form loop 130. In contrast to the previous embodiments, a serrated rack 190 is disposed between the opposed ends of the belt 188. The gear teeth 192 on rack 190 are dimensioned to receive the gear teeth on a pinion gear 194. Pinion gear 194 is secured to plate 182 using pin 196 which, in turn, is keyed to the shaft 148 extending from knob 146 (in shadow). As with the embodiment of FIG. 5, the interior surface 198 of belt 188 may either be smooth or serrated. During use, clockwise rotation of knob 146 causes rack 190 to be moved distally and away from pulley 184, thereby causing the organ held within the loop to be turned in the same direction as the knob 146 is rotated.

FIG. 8 shows an enlarged view of yet another embodiment for effecting rotation of an organ grasped within loop 130. Again, the cover plate is removed to show the inner working parts. In this view, the instrument frame 200, the slide member assembly 132, and the finger grip assembly 138 are all constructed in the manner of the corresponding portions of the embodiments of FIGS. 3 and 5. Although extending through tubular member 124 to form loop 130, as previously described, belt or cable 202 does not form a continuous loop. Instead, the opposed ends of belt 202 each terminate in a gear rack 204 and 206. A pinion gear 208 is rotatably mounted on slide plate 210 with pin 212 acting as an axle. Pin 212 is keyed to the shaft 148 extending from knob 146 (in shadow) and pinion gear 208 is disposed between racks 204 and 206, engaging each. The gear racks are placed within channels 214 and 216 to prevent migration as they are displaced proximally and distally. Clockwise rotation of knob 146 causes pinion gear 208 to be turned clockwise, engaging both racks. Rack 206 will be moved toward proximal end 114 as rack 204 moves toward distal end 116 of the handle, thus effectively rotating the grasping loop and any tissue held therein. Belt 202 may also be smooth or serrated.

In operation, tubular member 124 is inserted through an incision in a patient or through a laparoscopic trocar and advanced toward an internal organ. Slide member assembly 132 is pulled downward to disengage detent tooth 218 from serrated edge 220, then the assembly is moved distally to enlarge the portion of belt 202 exposed beyond the distal end of hub 126, thus slackening the loop 130. Loop 130 is positioned around the organ of choice, then slide member assembly 132 is pulled downward to once again disengage detent tooth 218 from serrated edge 220 on slide plate 210. The slide plate 210 is then moved proximally as thumb loop 132 is displaced to tighten loop 130 around the organ. Once again, the release of downward pressure locks the detent tooth 218 in edge 220 to prevent slipping. When it is desired to twist or rotate the organ, the surgeon will grasp and rotate knob 146. As previously disclosed, clockwise rotation of knob 146 will cause pinion gear 208 to also move clockwise, causing rack 204 to be advanced toward the distal end of the instrument. Simultaneously, rack 206 will be commensurately withdrawn toward the proximal end of the instrument. Simultaneous movement of racks 204 and 206 in opposite directions will impart rotation to loop 130 and friction between the inner surface of belt 202 and the external surface of the organ contained therein will cause the organ to rotate about an axis transverse to that of the instrument 110. The rotation now possible utilizing the present invention greatly assists the surgeon in exposing the base of the organ and various tissues lying thereunder, significantly decreasing the difficulty encountered in performing the procedure.

Figure 9:
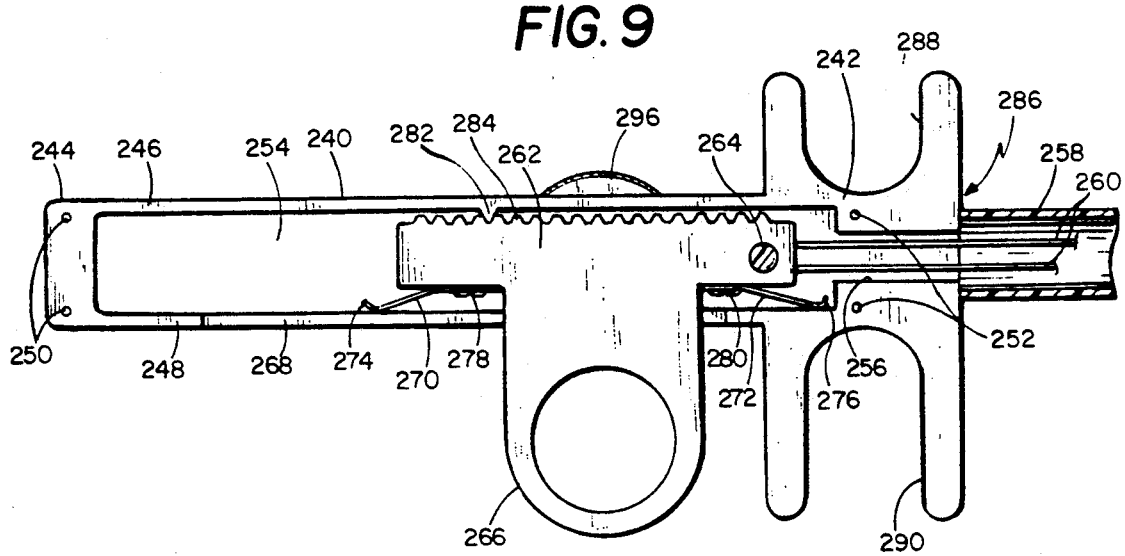
FIG. 9 is an enlarged, side elevation view of the proximal end of an alternative embodiment of the present invention with the cover plate removed.

FIG. 9 shows an enlarged view of an alternative embodiment of the proximal end of the handle member 12 of FIG. 1. Its individually molded pieces may be metal or any rugged, medical grade plastic. The instrument frame 240 has a distal end 242 and a proximal end 244, with a top 246 molded co-extensively with the bottom 248. Screw holes 250 and 252 are drilled, molded, or otherwise formed in instrument frame 240 to receive the screws which secure a pair of cover plates (FIG. 9). The instrument frame 240 is molded to further include a void or hollow region 254 between the top 246 and bottom 248. At the distal end 242, the frame 240 is molded to form a channel 256 between the void 254 and the elongated tubular member 258. The cable 260 may have a smooth surface or, for enhanced friction during grasping, it may be roughened. It extends from the slide member plate 26 through the channel 256 to form a loop. The ends of the cable 260 are secured to slide member plate 262 at screw 264. Extending from plate 262 is a thumb loop 266, which may be a separate molded piece glued to the plate or may be molded coextensively therewith. The bottom 248 of the instrument frame includes a slot 268, dimensioned to allow proximal and distal displacement of the thumb loop 266. Extending toward the instrument frame bottom 248 from the slide member plate 262 are a pair of leaf springs 270 and 272, which are angled at their ends 274 and 276 for enhanced tension. The leaf springs 270 and 272 are preferably made of phosphor-bronze and are held against the slide member plate 262 by screws 278 and 280. A detent tooth 282 projects inwardly from the top 246 of the instrument frame and is dimensioned appropriately to mesh with a serrated edge 284 that is included on the upper edge of plate 262. A finger grip assembly, generally designated 286, has slots 288 and 290 dimensioned to receive a surgeon's fingers and is molded to fit alongside instrument frame 240 and between the cover plates (not shown).

Figure 10:
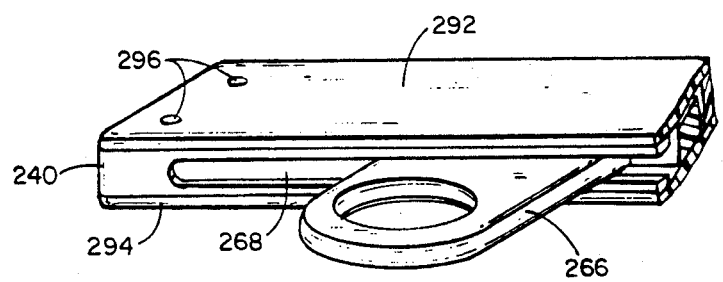
FIG. 10 is a partial, perspective, bottom view of the proximal end of the laparoscopic surgical instrument of FIG. 8.

The moveable thumb loop 266 is shown more clearly in FIG. 10. The screw holes 250 that are drilled or otherwise formed through instrument frame 240 extend also from cover plate 292 to cover plate 294. Thus, when the cover plates are secured, screws 296 enter through cover plate 292 and project through instrument frame 240. Cover plate 294 receives their threaded ends so both cover plates are immobilized. Similarly, when screws are inserted into holes 252, the finger grip assembly 286 is immobilized against the frame 240 and between the cover plates 292 and 294.

In operation, the surgical instrument shown in FIGS. 8 and 9 is used to grasp an organ or tissue in an analogous manner to the procedure described in reference to FIGS. 1 and 2. Furthermore, the instrument of FIGS. 8 and 9 may also be fitted with a rotator assembly 296, as shown in FIG. 4.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A method of using a surgical instrument having a grasping loop to treat tissue and organs, comprising the steps of:
    (a) inserting a surgical instrument into an incision in a patient, said surgical instrument having a handle means having a distal end and a proximal end for grasping by a surgeon, an elongated tubular member having a distal and a proximal end and a lumen extending therebetween, said proximal end of said elongated tubular member joined to said distal end of said handle means, a belt means disposed within said elongated tubular member and extending distally therefrom to form a closed loop for surrounding and grasping said tissue and organs, a slide means coupled to said belt means for causing said belt means to move proximally and distally to grasp said tissue and organs, and rotator means operatively coupled to said belt means for causing said closed loop of said belt means to rotate;
    (b) using said slide means to extend said belt means distally of said distal end of said tubular member to form a grasping loop having a diameter to surround tissue and internal organs;
    (c) retracting said slide means to tighten said grasping loop of said belt means around said tissue and internal organs;
    (d) rotating said tissue and internal organs about an axis transverse to said elongated tubular member using said rotator means while maintaining a fixed said diameter of said grasping loop.

2. The method of using a surgical instrument having a grasping loop, as recited in claim 1, and including the additional steps of:
    (e) treating said tissue and internal organs with medical instruments while holding said tissue and internal organs within said grasping loop;
    (f) severing said tissue and organs with medical instruments while holding said tissue and internal organs within said grasping loop; and
    (g) removing said grasped tissue and organs by withdrawing said surgical instrument from within said incision.

3. A surgical instrument for laparoscopic and endoscopic treatment of tissue and organs, comprising:
    (a) a handle member having a distal end and a proximal end;
    (b) an elongated tubular member having a distal end and a proximal end and a lumen extending therebetween, and joined at said proximal end to said distal end of said handle member;
    (c) belt means disposed within said lumen of said elongated tubular member and extending distally therefrom forming a grasping loop having a diameter for surrounding and grasping said tissue and organs;
    (d) manually operable slide means coupled to said belt means for causing said belt means to move proximally and distally to grasp said tissue and organs; and
    (e) rotator means operatively coupled to said belt means for causing said grasping loop of said belt means to rotate about an axis transverse to said elongated tubular member while maintaining a fixed said diameter of said grasping loop and while grasping said tissue and organs.

4. The surgical instrument of claim 3 wherein said belt means has first and second ends and said rotator means comprises:
    (a) a first rack and a second rack, each having an end, said first end of said belt means affixed to said end of the first rack and said second end of said belt means affixed to said end of the second rack, and
    (b) a pinion gear rotatably mounted on said manually operable slide means between and engaging said first and second racks.

5. The surgical instrument of claim 3 wherein said rotator means comprises:
(a) a rack defined along said belt means;
(b) a pinion gear journaled for rotation on said slide means for engaging said rack; and
(c) a pulley rotatably mounted on said slide means for maintaining tension on said belt means.

6. The surgical instrument of claim 3 wherein said rotator means comprises:
a drive roller journaled for rotation on said slide means.

7. The surgical instrument of claim 6, further including:
an idler roller rotatably mounted on said slide means and having said belt means disposed between said drive and idler rollers, rotation of said drive roller rotating said belt means.

8. A surgical instrument for laparoscopic and endoscopic treatment of tissue and organs, comprising:
(a) a handle member having a distal end and a proximal end;
(b) an elongated tubular member having a distal end and a proximal end and a lumen extending therebetween, said proximal end of said elongated tubular member joined to said distal end of said handle member;
(c) a belt means disposed within said lumen of said elongated tubular member and extending distally therefrom forming a grasping loop for surrounding and grasping said tissue and organs;
(d) manually operable slide means coupled to said belt means for causing said belt means to move pivotally and distally to grasp said tissue and organs, said slide means including detent means comprising a plurality of ratchet teeth formed on said slide means and at least one fixed tooth on said handle member for engaging said ratchet teeth, and
(e) means for normally biasing said ratchet teeth into engagement with said at least one fixed tooth of said handle member, wherein said ratchet teeth are retractable from said fixed tooth when said slide means is advanced to move said belt.

9. The surgical instrument of claim 8, wherein said slide means further includes:
a rigid, finger-engagable loop means extending from said slide means for causing said belt means to move proximally and distally, said slide means having a distal end affixed to said belt means.

10. The surgical instrument of claim 8, wherein:
said belt means further includes an inner surface that is roughened.

11. The surgical instrument of claim 8, wherein:
said belt means forms a continuous loop.

* * * * *